(12) United States Patent
Heino

(10) Patent No.: US 7,666,909 B2
(45) Date of Patent: Feb. 23, 2010

(54) ENHANCEMENT OF ALCOHOL METABOLISM

(76) Inventor: Pekka Heino, Lahnaruohontie 4 B 13, Helsinki (FI) FIN-00200

( * ) Notice: Subject to any disclaimer, the term of this patent is extended or adjusted under 35 U.S.C. 154(b) by 1039 days.

(21) Appl. No.: 11/105,022

(22) Filed: Apr. 13, 2005

(65) Prior Publication Data
US 2005/0182135 A1 Aug. 18, 2005

(51) Int. Cl.
*A61K 31/19* (2006.01)
*A61K 31/22* (2006.01)
(52) U.S. Cl. .................. 514/557; 514/546; 424/439
(58) Field of Classification Search .......... 514/557, 514/546; 424/439
See application file for complete search history.

(56) References Cited

U.S. PATENT DOCUMENTS 6,117,868 A * 9/2000 Pfirrmann ............... 514/222.5

FOREIGN PATENT DOCUMENTS

EP 0 508 324 10/1992

OTHER PUBLICATIONS

Eur. J. Biochem. vol. 30, 1972, Herluf I.D. Thieden et al: Effect of Fructose and Glyceraqldehyde on Ethanol Metalbolism in Human Liver and in Rat Liver:, pp. 250-261.

Folia Micobiol, vol. 46, No. 1, 2001, K. Lesova et al: "OR-1-a Mixture of Esters of Glyceric Acid Produced by Penicillium funiculosum and ItsAntitrypsin Activity", pp. 21-23.

The Merck Index, Twelfth Edition, Sundan Budavari, "An Encyclopedia of Chemicals, Drugs, and Biologicals". 1996, p. 4493, abstract 4492.

* cited by examiner

*Primary Examiner*—Ardin Marschel
*Assistant Examiner*—Zohreh Vakili
(74) *Attorney, Agent, or Firm*—Skinner & Associates

(57) ABSTRACT

D-glyceric acid has been found to enhance alcohol metabolism and thereby prevent adverse effects of alcohol consumption. D-glyceric acid is administered concurrently with alcohol, to accelerate the elimination of the alcohol from the body. D-glyceric acid is converted into D-glyceraldehyde and further into glycerol in reactions catalysed by NADH-aldehyde dehydrogenase and NADH-alcohol dehydrogenase complexes, which are produced in excess during alcohol oxidation, in the cells of alcohol-metabolising tissues. In these reactions, the NADH complexes become NAD-aldehyde dehydrogenase and NAD-alcohol dehydrogenase complexes. These complexes in turn accelerate the oxidation of alcohol, which is paralleled by enhancement of acetaldehyde oxidation to metabolically harmless acetic acid. D-glyceric acid or its salt or ester is used for the manufacture of a pharmaceutical preparation for enhancing the metabolism of alcohol. A method of enhancing the metabolism of alcohol in a subject by administering said compounds an effective amount of D-glyceric acid or its salt or ester is disclosed. An oral or parenteral preparation comprising said compounds is also disclosed.

14 Claims, 3 Drawing Sheets

ENHANCEMENT OF ALCOHOL METABOLISM

FIELD OF THE INVENTION

The present invention relates to a compound capable of enhancing alcohol metabolism and thereby capable of preventing adverse effects of alcohol consumption. More precisely the present invention is directed to the use of D-glyceric acid or its salt or ester for the manufacture of a pharmaceutical preparation for enhancing the metabolism of alcohol. The invention is also directed to a method of enhancing the metabolism of alcohol in a subject comprising administering an effective amount of one or more compounds selected from the group consisting of D-glyceric acid and its salts and esters to a subject in need thereof. An oral or parenteral pharmaceutical preparation comprising said compounds is disclosed.

BACKGROUND OF THE INVENTION

It is known that 5% of the ethyl alcohol i.e. ethanol (hereinafter alcohol), $C_2H_5OH$, ingested by a human being is excreted unchanged while the remaining 95% is degraded to acetaldehyde (hereinafter AcA), $CH_3CHO$, in the cells of alcohol-metabolising tissues, mainly the liver. This reaction (Reaction 1) takes place in the cytoplasm of hepatocytes and is catalysed by the local enzyme alcohol dehydrogenase, ADH. The reaction uses one molecule of the coenzyme nicotinamide-adenine dinucleotide, NAD, per each molecule of alcohol:

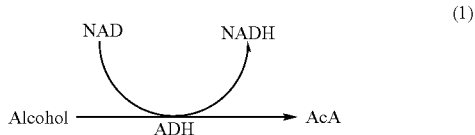

(1)

During the reaction, NAD and ADH form an enzyme-coenzyme (ADH-NAD) complex, with NAD being concurrently reduced to NADH. The NADH is then detached, and the ADH is ready to repeat the reaction by accepting a new NAD molecule. The cell has a limited capacity to oxidise NADH back to NAD, which determines the maximum velocity of the reaction. A normal liver metabolises alcohol at the rate of about 8 g/h. The rate is independent of the concentration of alcohol in blood. There is an excess of ADH enzyme for the reaction.

The AcA molecules converted from alcohol move into cytoplasmic organelles known as mitochondria where they are oxidised to acetic acid, $CH_3COOH$, in a reaction (Reaction 2) catalysed by the enzyme aldehyde dehydrogenase, ALDH:

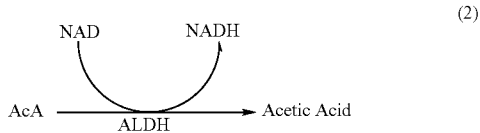

(2)

In this reaction, too, one molecule of the coenzyme NAD is reduced to NADH. Both the latter and the NADH previously accumulated in the cytoplasm are reoxidised to NAD in the mitochondrial respiratory chain at the maximum capacity of this system. The maximum capacity of the mitochondrial respiratory chain depends on the overall level of metabolism of the body.

The above-described process of alcohol metabolism is illustrated in FIG. 1.

The metabolically harmless acetic acid, derived from alcohol through AcA, is oxidised to carbon dioxide and water mainly in extrahepatic tissues.

The capacity of cells to oxidise NADH back to NAD is exceeded during alcohol degradation according to Reactions 1 and 2. As a result, cells accumulate an excess of NADH compared with NAD. This change in the cellular oxidation-reduction equilibrium, which always takes place in connection with alcohol metabolism, causes inhibition of NAD-mediated enzyme reactions typical to the normal metabolism of the hepatocyte. The most important of these inhibited systems is the citric acid cycle. A positive NADH/NAD ratio, leading to inhibition of the citric acid cycle, is considered the most important reason for the development of alcohol-induced fatty liver.

In a normal liver, 99% of the alcohol brought by blood circulation is metabolised to acetic acid. The remaining 1% is released as AcA into the circulation. So, the capacity of the alcohol-metabolising tissues is not fully sufficient to oxidise all the AcA formed in Reaction 1 to acetic acid according to Reaction 2. This is evident, for instance, from the fact that the venous blood flowing out of the liver during alcohol metabolism carries a 15-μM concentration of AcA (Eriksson and Fukunaga 1992).

The acute toxicity of AcA (mouse $LD_{100}=0.75$ g/kg) is severalfold compared with that of alcohol (mouse $LD_{70}=6.5$ g/kg).

As explained above, during alcohol use about 1% of AcA normally "escapes" Reaction 2 in the liver and enters the blood circulation at the rate of about 1 mg/min (60 mg/h). If the alcohol consumption is sufficient to maintain a concentration of alcohol in blood for 24 hours (200 g of alcohol is enough, i.e. the amount contained in a half-liter of distilled spirit), the amount of AcA released into the circulation is on average 1.5 g. As a single dose, this amount of AcA would be enough to kill 100 mice each weighing 20 g.

Still larger amounts of AcA than those mentioned above are released into the blood circulation in case of impaired ALDH activity. A reduction as small as 10% in the capacity of hepatic ALDH triples the amount of AcA leaked into the circulation.

ALDH can be inhibited by certain drugs, such as disulfiram (Antabuse®). In a person on disulfiram therapy, ingestion of a few grams of alcohol will produce very unpleasant symptoms lasting up to several hours. The symptoms include headache and a flushed skin. Dyspnoea and nausea are also common, as are tachycardia and hypotension. The symptoms are due to AcA accumulation in the body.

Heavy use of alcohol is followed by hangover, a familiar consequence of alcohol intoxication. A person fearing hangover may seek to prolong his/her use of alcohol. The fact that efforts to develop an adequate pharmacological means of treating hangover have so far been unsuccessful may also contribute to such behaviour. Alleviation of hangover has been attempted by vitamins and trace elements (cf. U.S. Pat. No. 4,496,548). A major part of hangover symptoms may be due to the toxic effects of AcA.

Biochemical and medical research suggests a major role for AcA in the development of alcohol dependence. These conclusions are based on the changes that AcA induces in the structures of cerebral neurotransmitters. AcA has also been found to inhibit enzymes involved in protein synthesis and to alter the immunological properties of tissues. Through such mechanisms, AcA may in fact play a more significant role than alcohol in the aetiology of many alcohol-related diseases, such as brain damage and hepatic cirrhosis and also compulsive drinking itself.

As explained above, it has become clear that elevation of the NADH/NAD ratio, which suppresses normal metabolism in alcohol-metabolising tissues, and the release and accumulation of AcA in the systemic circulation and thereby in the entire body are major mechanisms in the development of alcohol-related health problems.

In view of the above-mentioned facts, AcA-binding compounds have been deployed to reduce the amount of AcA released into the systemic circulation and to lessen the consequences of such release. These compounds include the sulphur-containing amino acids cysteine and methionine. Oral administration of methionine to experimental subjects during alcohol drinking has yielded 20% reductions in blood AcA concentrations (Tabakoff et al. 1989). It should be noted, however, that methionine-bound AcA may later detach, thus obliterating the minor benefit achieved. Furthermore, methionine and other similar substances do not affect the rate of alcohol metabolism, nor the NADH/NAD ratio.

In addition to the above-mentioned methods, it has been proposed that the adverse health effects of alcohol might be reduced with agents that modify the rate of alcohol metabolism:

Both the amount of AcA released from the liver and the NADH/NAD ratio can be lowered by 4-methylpyrazole, 4-MP. This is an ADH inhibitor which slows down Reaction 1 (see page 1). As a result, the production of AcA is reduced and, with less substrate, Reaction 2 becomes more effective allowing more extensive conversion of AcA to acetic acid. Owing the diminished total capacity of the reactions, there is no intracellular accumulation of NADH. 4-MP is useful in special circumstances requiring deceleration of alcohol metabolism, e.g. in the management of methanol poisoning. 4-MP is not suited to addressing the aforementioned problem of AcA accumulation. Because of its decelerating effect on alcohol elimination, it would be impossible to use in conjunction with conventional alcohol drinking (risk of alcohol poisoning).

The accelerating effect of fructose on the rate of alcohol elimination has been known for a long time (Crownover et al. 1986). The elimination rate may be enhanced by up to 20% but this requires large doses (1-5 g/kg) to be taken together with the alcohol. Trials have been conducted of the prevention of hangover symptoms by means of fructose, without tangible benefit. It has been established that acceleration of alcohol metabolism by fructose is effected specifically through Reaction 1. This method of increasing the rate of alcohol metabolism leads to the formation of a corresponding amount of AcA which the cell is unable to metabolise to acetic acid. This is reflected as a corresponding elevation of AcA concentration in the blood flowing out of the liver (Eriksson and Fukunaga 1992).

It has also been known for a long time that D-glyceraldehyde (hereinafter D-GA; see FIG. 3, "Metabolism of fructose", (Harper et al. 1977)), a metabolite of fructose, has an accelerating effect on alcohol metabolism (Thieden et al. 1972). The effect of D-GA on the metabolism of AcA is similar to that of fructose, in that the accelerating effect on alcohol metabolism takes place via Reaction 1 and not via Reaction 2. Akin to fructose, D-GA therefore tends to cause AcA accumulation.

U.S. Pat. No. 4,450,153 presents a solution whereby blood alcohol concentration can be rapidly reduced using an alcohol oxidase enzyme isolated from certain species of yeast. Said enzyme degrades alcohol to AcA in the extracellular space. This causes large amounts of AcA to enter the blood circulation and, consequently, a risk of AcA poisoning.

The present invention offers substantial remediation of the shortcomings presented above.

SUMMARY OF THE INVENTION

The present invention provides the use of D-glyceric acid or its salt or ester for the manufacture of a pharmaceutical preparation for enhancing the metabolism of alcohol.

The invention further provides a method of enhancing the metabolism of alcohol in a subject comprising administering an effective amount of D-glyceric acid or its salt or ester to a subject in need thereof.

The invention still further provides an oral or parenteral pharmaceutical preparation for enhancing the metabolism of alcohol comprising one or more compounds selected from the group consisting of D-glyceric acid and its salts and esters.

Some of the preferred embodiments of the invention are set forth in the dependent claims.

DETAILED DESCRIPTION OF THE INVENTION

Figure 1:
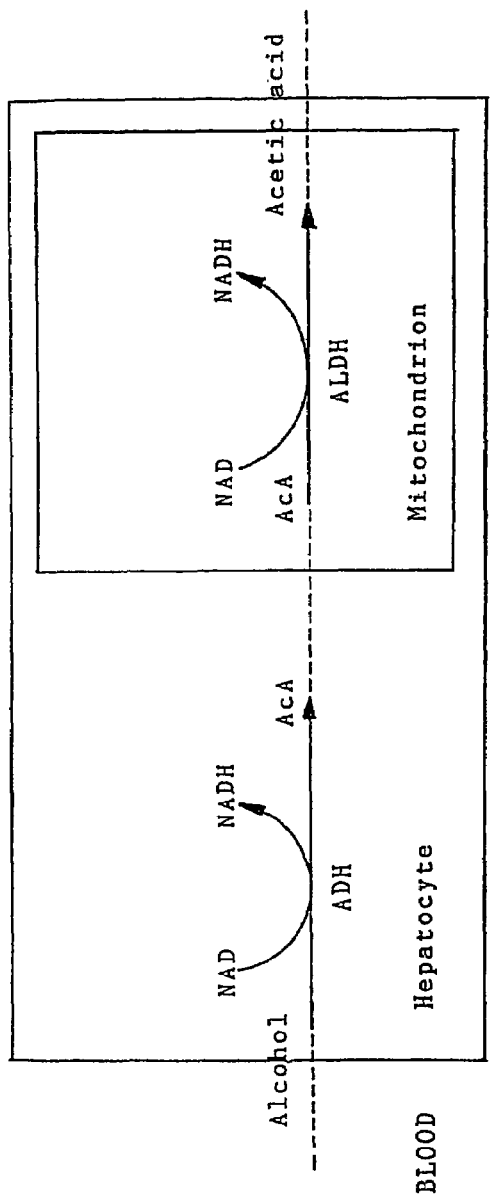
FIG. 1 illustrates the metabolism of alcohol.

The operation and principle of the invention are presented below.

In accordance with the invention, D-glyceric acid (hereinafter D-GLAC), i.e the dextrorotatory optical isomer of glyceric acid, is used to enhance the metabolism of alcohol in the body. It is a commonly known phenomenon in physiology and biochemistry that the body is able to utilise physiologically only one isomer of organic compounds that contain asymmetric carbon atoms and therefore exist as both D and L isomers. The other isomer is physiologically inert. In consequence, the physiologically active isomer of a compound and its physiologically inert counterpart have different metabolic routes. This is also true for glyceric acid. The metabolic route and hence the physiological characteristics of L-glyceric acid, i.e. the glyceric acid isomer that rotates the plane of polarised light to the left, differ completely from those of D-GLAC, the subject of the present invention (cf. Bonham et al. 1977). Therefore, D-GLAC and L-glyceric acid also differ in their pharmacological properties.

"Glyceric acid" is mentioned as a component of the pharmaceutical compositions described, for instance, in documents U.S. Pat. No. 4,380,549, EP 775486 and WO 96/11572. The therapeutic indication of each of the compositions described in these documents differs from the one in the present invention. Further said documents do not mention, or provide a basis for deducing, which of the optical isomers of glyceric acid—D-GLAC or L-glyceric acid—constitutes the active substance in the particular invention. This issue is relevant since, as pointed out above, each of the two optical isomers of glyceric acid has its own pharmacological properties. EP 508 324 discloses topical compositions comprising 2-hydroxycarboxylic acids including glyceric acid for alleviating signs of dermatological aging. Lesova et al. 2001 disclose a mixture of esters of glyceric acid produced by *Peni-* cillium funiculosum. The mixture behaved as a non-competitive trypsin inhibitor. Penicillia are known to produce D-GLAC from the DL-form. None of the cited references teaches or suggests an alcohol metabolism enhancing effect of D-GLAC or its oral or parenteral use therefore.

D-GLAC is a syruplike, weakly acid compound that is readily soluble in water and alcohol and can be prepared by oxidation of glycerol. D-GLAC can be liberated from its commercially available calcium salt by simple treatment with dilute hydrochloric acid. Being an organic acid, D-GLAC is also capable of forming esters. D-GLAC can be liberated from its esters, for instance, by esterase enzymes. In the human body, these enzymes are present in the wall of the small intestine where they split esterified nutrients into a form that can be absorbed from the digestive tract.

D-GLAC is produced during normal sugar metabolism in the human body. Its energy content is 17 kJ/g which the body is able to utilise. For the purpose addressed by the present invention, D-GLAC may be preferably administered orally in the form of acid or a pharmaceutically or physiologically acceptable salt or ester. The possible dosage forms include syrup, powder, tablets, capsules, etc. It can also be administered in alcoholic or other beverages or in a food product or as part of one.

Figure 3:
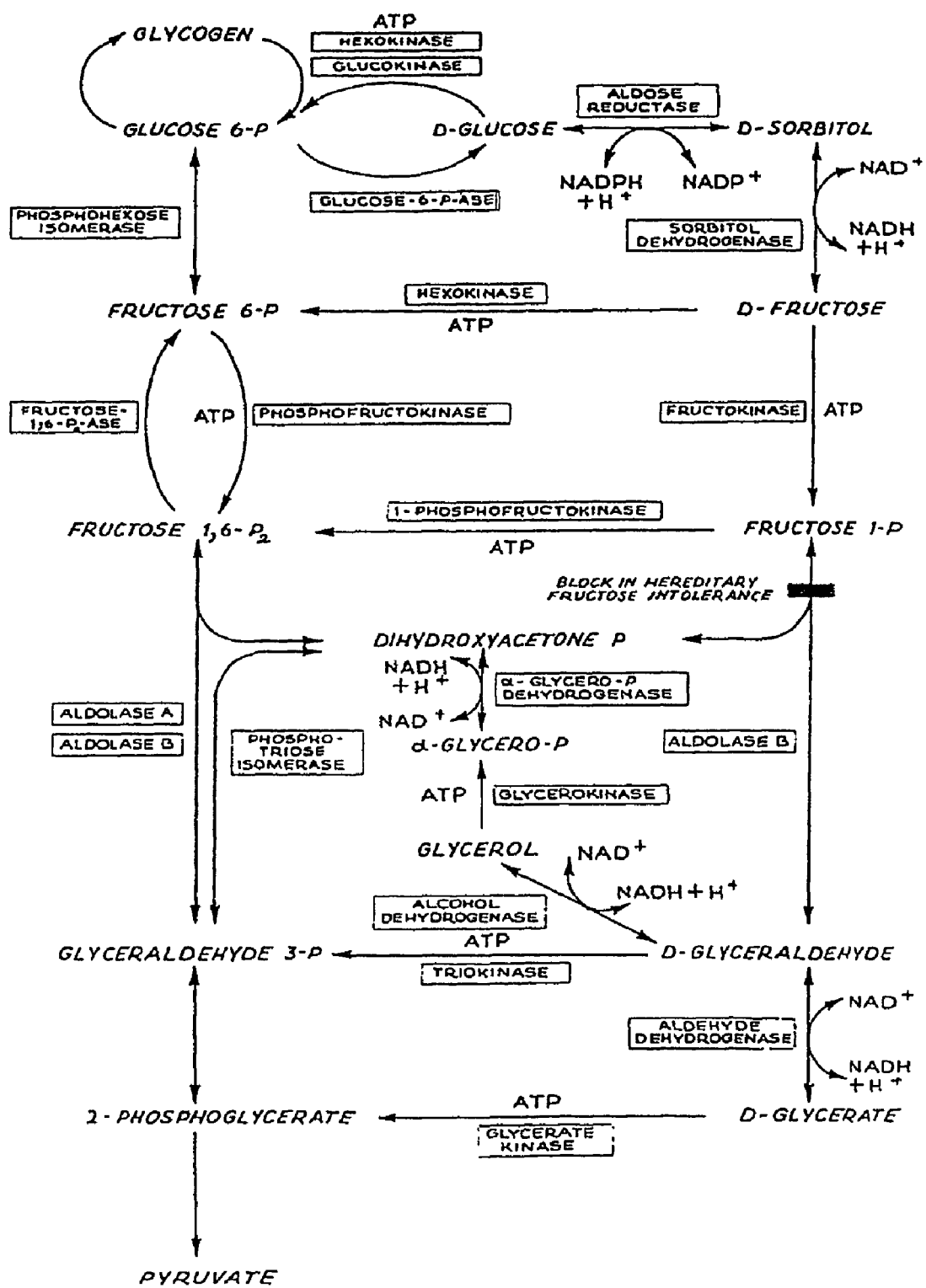
FIG. 3 illustrates the metabolism of fructose.

FIG. 3 shows that D-GLAC arises from D-GA in a reaction catalysed by ALDH, and D-GA in turn arises from glycerol in a reaction catalysed by ADH. Both reactions take place in alcohol-metabolising tissues, specifically in the liver.

The structural formulas of glycerol (a), D-GA (b) and D-GLAC (c) are presented below:

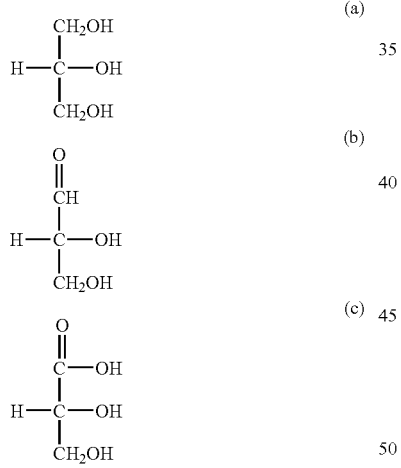

Glycerol is metabolised to D-GA in an ADH-catalysed reaction as follows (Reaction 3):

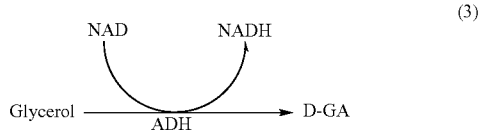

The reaction uses an equimolar amount of NAD which is reduced to NADH.

D-GA is metabolised to D-GLAC in an ALDH-catalysed reaction as follows (Reaction 4):

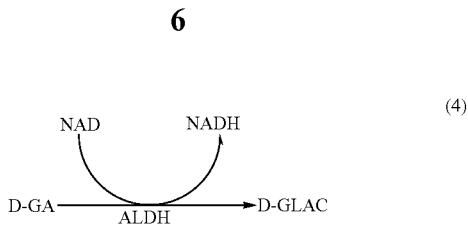

This reaction, too, uses the coenzyme NAD which is converted into NADH.

FIG. 3 shows that both Reaction 3 and Reaction 4 are equilibrium reactions, in other words, they can also proceed in the opposite direction.

When the invention is implemented by administering D-GLAC to humans or other mammals, the compound is transported in the blood circulation to alcohol-metabolising tissues. Since this substance has no other metabolic pathways, and it is administered much in excess of physiological amounts, it will undergo conversion into D-GA in Reaction 5 which is the reverse reaction of Reaction 4:

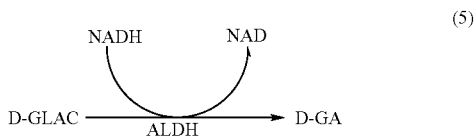

This reaction uses the coenzyme NADH which is oxidised to NAD.

Since the amount of D-GLAC given is much in excess of the physiological amount, the amount of NADH needed is also in excess of the physiological requirement.

A situation where there is an ample supply of NADH arises when the cell concerned metabolises, in addition to D-GLAC, also alcohol according to Reaction 2. Together, these reactions can be described as follows (Reaction 6):

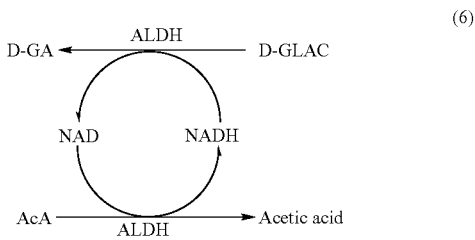

The two substrates, AcA and D-GLAC, do not compete for the common enzyme, ALDH, because AcA is able to utilise the enzyme only when the latter is complexed with NAD, and D-GLAC is able to utilise the enzyme only as an ALDH-NADH complex. When the previously mentioned Reaction 2 is taking place in the absence of D-GLAC, some of the enzyme will be present as an ALDH-NADH complex which cannot be used to oxidise AcA to acetic acid. With the introduction of D-GLAC as a second substrate, the enzyme-bound NADH will be immediately oxidised to NAD in conjunction with the conversion of D-GLAC into D-GA. The NAD thus formed is available to be used in Reaction 2. Thus, the enzymatic capacity of ALDH with regard to AcA will increase and the output of Reaction 2 will be enhanced by a molar amount corresponding to the consumption of D-GLAC.

This reveals the advantageousness of the approach applied in the present invention.

Despite the acceleration of Reaction 2, no excess of NADH arises since NADH is simultaneously used for converting D-GLAC into D-GA (Reaction 5).

The D-GA thus formed is then metabolised either to D-glyceraldehyde-3-phosphate in a reaction catalysed by the enzyme triokinase or to glycerol in a reaction catalysed by ADH (cf. FIG. 3). The former pathway is unidirectional and requires the energy of one molecule of adenosine triphosphate.

The latter metabolic alternative, a pathway leading to the formation of glycerol, utilises NADH as coenzyme according to Reaction 7:

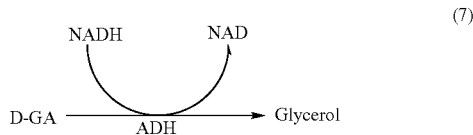

(7)

D-GA is directed onto this metabolic pathway (which is the reverse reaction of Reaction 3) by the oxidation of alcohol to AcA according to Reaction 1 which produces an excess of NADH. The total reaction can be described as follows (Reaction 8):

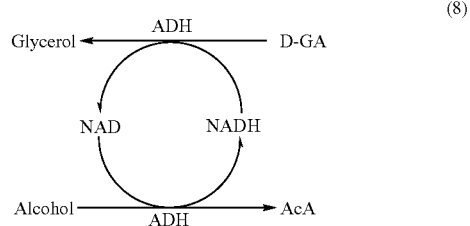

(8)

As shown in FIG. 3, the glycerol is further metabolised to α-glycerophosphate in an ATP-mediated reaction and then through various intermediate steps to glucose.

Reaction 8 indicates that the conversion of alcohol into AcA is accelerated in the same molar ratio as glycerol is formed—again without the production of any excess NADH. Thus, the situation is similar to Reaction 6 where D-GLAC accelerates the conversion of AcA into acetic acid, albeit with a quantitative difference: the volume of D-GA, i.e. the substrate that enters Reaction 8 and accelerates the conversion of alcohol into AcA, is smaller than that of D-GLAC, the corresponding substrate for Reaction 6. This is due to some of the D-GA formed being directed onto the previously mentioned second pathway. To recapitulate: the capacity of Reaction 1 is enhanced but that of Reaction 2 is enhanced even more.

When the rate of alcohol elimination from the body is increased by administration of D-GLAC according to the present invention, the acceleration of alcohol oxidation is paralleled by enhancement of AcA oxidation to acetic acid. The latter compound is metabolically harmless and is further degraded to carbon dioxide and water. In accordance with the invention, therefore, alcohol metabolism is enhanced in a way which allows "cleaner" combustion of alcohol in the body, that is, alcohol combustion with fewer adverse health effects than would otherwise be possible.

Alone the fact that the rate of elimination of alcohol introduced into the body is increased is an important benefit afforded by the present invention.

Figure 2:
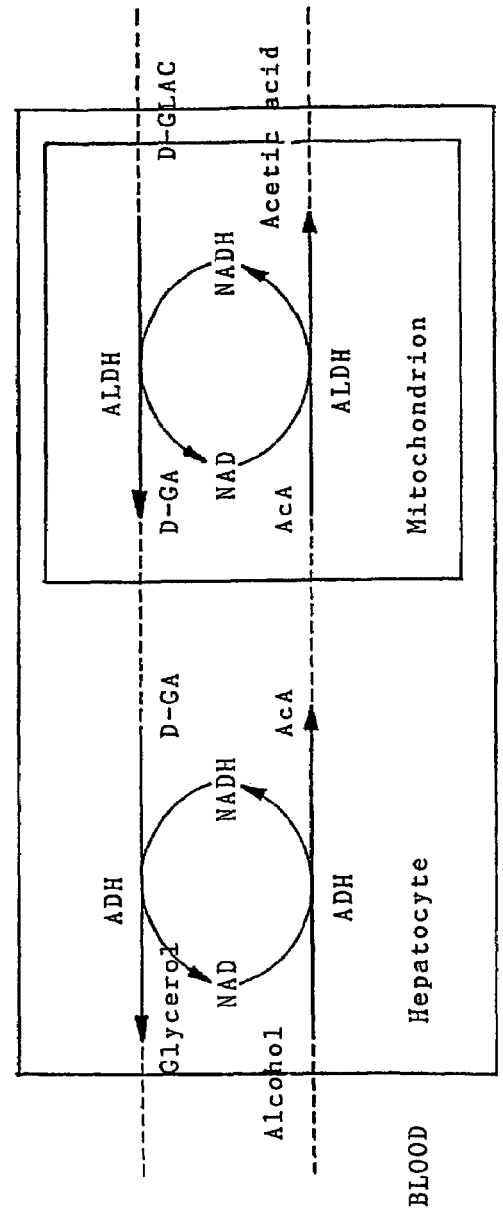
FIG. 2 illustrates the metabolism of alcohol in the presence of D-glyceric acid (D-GLAC).
Figure 4:
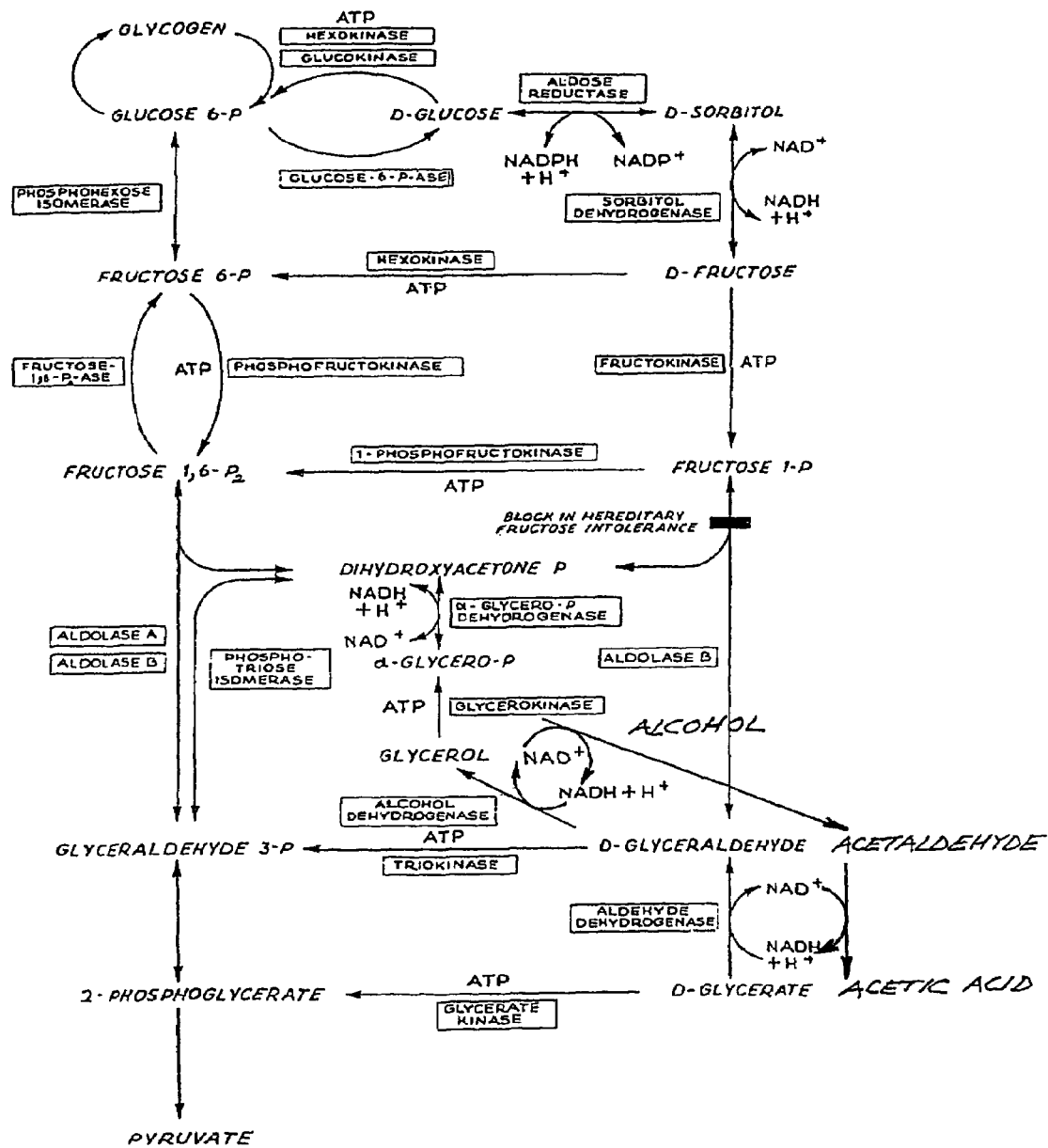
FIG. 4 illustrates the principle of the present invention.

The principle of the invention is illustrated in FIG. 4 and schematically in FIG. 2.

In accordance with the invention, D-GLAC is preferably administered orally in its acid and/or salt and/or ester form. It is common knowledge that the salts of weak acids—such as D-GLAC—are converted into acid form in the acidic environment prevalent in the stomach and, furthermore, that the ester bonds of the esters of these compounds break up as a result of the action of the esterases present in the intestinal wall, thus liberating the parent compound, in our case D-GLAC. The acid form of D-GLAC is syruplike in consistency and thus suited for oral administration as a syrup, a solution or in capsules. Apart from these dosage forms, the salts and esters of D-GLAC are suited for oral ingestion in powder or tablet formulations. As required, generally approved pharmaceutical or physiological excipients may be used in the preparations. A suitable dose of D-GLAC in acid, salt or ester form in connection with the use of alcohol is 1 to 2 g per hour by any of the above-mentioned methods of administration as long as there is alcohol in the bloodstream. The pharmaceutically acceptable acid and salt forms of D-GLAC are also suited for parenteral administration. Such administration would be preferable in cases of heavy alcohol intoxication. In these instances, Ringer's solution or 5% glucose solution containing D-GLAC in acid form, neutralised in the solution by D-GLAC salt, is preferred. Here a suitable total amount of D-GLAC and its salt could be 30 g/l, providing 3 to 15 g D-GLAC per hour at administration rates of 100-500 ml/h.

The present invention is illustrated by the following non-limiting examples.

EXAMPLE 1

The formation of acetic acid from AcA, mediated by the NAD produced in the reduction of D-GLAC, as described in Reaction 6 above, was demonstrated for the first time.

320 mg (3 mmol) of D-GLAC, liberated from the commercially obtained hemicalcium salt (Sigma-Aldrich) with sulphuric acid, was added in 2 ml of water to 30 ml of 0.25 mM potassium dihydrogen phosphate buffer solution (pH 6.865). Immediately prior to this, 13.2 mg (0.3 mmol) of AcA, 2 mg (5 units) of lyophilised ALDH and 210 mg (3 mmol) of NADH had been added to the buffer on ice. The solution was stirred for 6 hours. Its acidity was then increased to pH 3 by addition of 1 M phosphoric acid ($H_3PO_4$) one drop at a time. The solution was then subjected to continuous ether extraction for 6 hours, after which it was concentrated to 5 ml and analysed by gas chromatography.

A Micromat gas chromatograph equipped with a column and a flame ionisation detector was used. The column was a 30 cm×0.32 cm i.d. PE-Wax (N 931-6413) packed with polyethyleneglycol (PEG) (Perkin Elmer). Helium was used as carrier gas. The injector temperature was set at 200° C. and the detector temperature at 240° C.

The oven was so programmed that the column operated at 40° C. for the first 15 minutes after sample injection, and the column temperature was then increased at 15° C. per minute to the final temperature of 230° C. which was then maintained for the last 10 minutes.

An analysis of the chromatograms showed that acetic acid had been formed its retention time being 783 S. The result was verified using a commercial acetic acid preparation (Baker Analyzed Reagent) as reference.

EXAMPLE 2

The effect of D-GLAC on alcohol metabolism was studied in 80 adult male rats weighing 210-440 g (alcohol non-addicted, ANA rats, Alcohol Research Unit, National Public Health Institute, Helsinki). 40 animals were fasted for 12 hours before the experiment, and 40 were fed normally.

In the experiment, each rat received intraperitoneally an intoxicating single dose of alcohol (1.2 g/kg, 10% w/v) in physiological saline.

In addition to alcohol, half the rats (20 fasted and 20 non-fasted rats) received the hemicalcium salt of D-GLAC (Sigma-Aldrich) dissolved in said alcohol dose (0.5 g/kg, 5% w/v).

Blood samples were drawn from the saphenous vein of the tail of each rat before, 1 hour after and 2 hours after the administration of alcohol and D-GLAC. The blood samples were then analysed by headspace gas chromatography.

The results are presented in Table 1.

TABLE 1

| EFFECT OF D-GLYCERIC ACID ON BLOOD ALCOHOL LEVEL | | | | |
|---|---|---|---|---|
| Dose | Time[1] | Fasting | Blood alcohol concentration (mM)[2] | |
| (g/kg) | (h) | (+/−) | D-GLAC + (N) | D-GLAC − (N) |
| 0.5 | 1 | − | 21.8∀0.5 (20)[3****] | 26.8∀0.7 (20) |
| 0.5 | 1 | + | 24.4∀0.8 (20)[3,4****] | 29.8∀0.6 (20)[4****] |
| 0.5 | 2 | − | 12.5∀0.6 (20)[3****] | 18.0∀0.9 (20) |
| 0.5 | 2 | + | 16.6∀0.8 (20)[3,4****] | 22.2∀0.5 (20) |

[1]time from alcohol administration;
[2]mean ∀ SEM;
[3]comparison between glycerate + and glycerate −;
[4]comparison between fasting + and fasting −;
*$P < 0.05$;
***$P < 0.001$ Among both the fasted and nonfasted rats, the group that had received D-GLAC had on average 20% lower blood alcohol concentration than the corresponding control group that had received no D-GLAC but had received the same amount of alcohol as the corresponding D-GLAC group.

It could be concluded that D-GLAC had essentially enhanced the metabolism of alcohol.

NON-PATENT REFERENCES CITED

Bonham J R, Stephenson T J, Carpenter K H, Rattenbury J M, Cromby C H, Pollitt R J, Hull D: D(+)-Glyceric Aciduria: Etiology and Clinical Consequences. Pediatric Research, Vol 28, No 1, 1990, p. 41.

Crownover B, La Dine J, Bradford B, Glassman E, Forman D, Schneider H, Thurman R G: Activation of Ethanol Metabolism in Humans by Fructose: Importance of Experimental Design. The Journal of Pharmacology and Experimental Therapeutics, Vol 236, No 3, 1986, p. 574-579.

Eriksson C J P, Fukunaga T: Human Blood Acetaldehyde (Update 1992), Alcohol & Alcoholism, Suppl. 2, 1992, p. 9-25.

Harper H A, Rodwell V W, Mayes P A: Review of Physiological Chemistry, 16 p., Lange Medical Publications, Los Altos, Calif., 1977, p. 274.

Lesová, K. et al. Folia Microbiologica, 2001, vol. 46, no 1, p. 21-23, Abstract.

Tabakoff B, Eriksson C J P, Wartburg J-P: Methionine Lowers Circulating Levels of Acetaldehyde after Ethanol Ingestion. Alcoholism: Clinical and Experimental Research, Vol. 13, No. 2, 1989, p. 164-171.

Thieden H, Grunnet N, Damgaard S E, Seftoft L: Effect of Fructose and Glyceraldehyde on Ethanol Metabolism in Human Liver and in Rat Liver, European Journal of Biochemistry, Vol. 30, 1972, p. 250-261.

The invention claimed is:

1. A method of enhancing the metabolism of alcohol in a subject comprising the step of administering an effective amount of one or more compounds selected from the group consisting of D-glyceric acid and its salts to a subject in need of enhancing the metabolism of alcohol.

2. The method according to claim 1, comprising administering a pharmaceutically effective amount of one or more compounds selected from the group consisting of D-glyceric acid and its salts, as the only active substance(s).

3. The method according to claim 2, comprising administering a pharmaceutically effective amount of one or more compounds selected from the group consisting of D-glyceric acid and its salts, as the sole ingredient(s).

4. The method according to claim 1, comprising administering a pharmaceutical preparation comprising one or more compounds selected from the group consisting of D-glyceric acid and its salts, and a pharmaceutically acceptable excipient.

5. The method according to claim 1, comprising administering the one or more compounds via an oral preparation in the form of a solution, syrup, powder, capsule or tablet.

6. The method according to claim 1, comprising administering the one or more compounds via a parenteral solution.

7. The method according to claim 1, comprising administering the one or more compounds via a beverage or a food product.

8. An oral or parenteral pharmaceutical preparation for enhancing the metabolism of alcohol comprising one or more compounds selected from the group consisting of D-glyceric acid and its salts.

9. The method according to claim 5, wherein the effective amount is 1 to 2 grams D-glyceric acid or its salt, administered per hour.

10. The method according to claim 6, wherein the effective amount is 3-15 grams D-glyceric acid administered per hour.

11. The oral pharmaceutical preparation of claim 8, comprising 1-2 grams D-glyceric acid or its salt.

12. The parenteral pharmaceutical preparation of claim 8, comprising 30 grams per liter D-glyceric acid and its salt.

13. The parenteral pharmaceutical preparation of claim 8, further comprising Ringer's solution or 5% glucose solution.

14. A preparation for enhancing the metabolism of alcohol in a subject, the preparation comprising a physiologically effective amount of D-glyceric acid, or its salt, the preparation being selected from the group consisting of an oral or parenteral solution, a syrup, a powder, a capsule, a tablet, a beverage, a food product, and a food supplement.

\* \* \* \* \*